United States Patent [19]
Kokubo

[11] Patent Number: 5,609,633
[45] Date of Patent: Mar. 11, 1997

[54] TITANIUM-BASED BONE-BONDING COMPOSITES HAVING INVERTED CONCENTRATION GRADIENTS OF ALKALI AND TITANIUM IONS IN A SURFACE LAYER

[75] Inventor: Tadashi Kokubo, Kyoto, Japan

[73] Assignee: The Foundation for Promotion of Ion Engineering, Kyoto, Japan

[21] Appl. No.: 338,171

[22] Filed: Nov. 9, 1994

[30] Foreign Application Priority Data

Nov. 9, 1993 [JP] Japan .................................. 5-304659

[51] Int. Cl.$^6$ ........................................................ A61F 2/28
[52] U.S. Cl. ............................ 623/16; 606/76; 523/113; 523/115
[58] Field of Search .............................. 623/16; 523/113, 523/115; 606/76, 77

[56] References Cited

U.S. PATENT DOCUMENTS 4,801,300  1/1989  Kurze et al. ............................... 606/76
4,965,088  10/1990  Shimamune et al. ...................... 623/16

OTHER PUBLICATIONS

Kasemo, Biocompatibility of Titanium Implants: Surface Science Aspects, Jun. 1983, J. of Pros. Dent., vol. 49, No. 6, pp. 832–837.

"An Introduction to Bioceramics", Hench et al., *World Scientific*, vol. 1, (1993), pp. 223–238.

"The role of hydrated silica, titania, and alumina in inducing apatite on implants", Li et al., *Journal of Biomedical Materials Research*, vol. 28, (1994), pp. 7–15.

"Surface Preparation and Corrosion Behavior of Titanium Alloys for Surgical Implants", Fraker et al., *ASTM Special Technical Publication*, vol. 796, (1981), pp. 206–219.

"The Growth Kinetics and Optical Properties of Films Formed Under Open Circuit Conditions on a Titanium Surface in Potassium Hydroxide Solutions", *Corrosion Science*, vol. 33 (1), (1992), pp. 153–164.

*Primary Examiner*—Paul B. Prebilic
*Attorney, Agent, or Firm*—Millen, White, Zelano & Branigan, P.C.

[57] ABSTRACT

A bone substitute, which provides both the fracture toughness of titanium or titanium alloys and the bioactivity of apatite, wherein titanium or titanium alloys and apatite are tightly adhered, is produced by soaking a substrate of titanium or titanium alloy in an alkaline solution to form a layer comprising amorphous alkali titanate, followed by the heating of the said substrate up to at most the titanium or titanium alloy transition temperature so as to form a stabilized amorphous alkali titanate layer and a sufficient concentration gradient of alkali and titanium ions to permit the growth of apatite thereon from solutions containing apatite-containing ions.

14 Claims, 1 Drawing Sheet

TITANIUM-BASED BONE-BONDING COMPOSITES HAVING INVERTED CONCENTRATION GRADIENTS OF ALKALI AND TITANIUM IONS IN A SURFACE LAYER

BACKGROUND OF THE INVENTION

This invention relates to a material suitable for use as a bone substitute and the manufacturing method thereof, and in particular to a bone substitute useful for repairing body parts subjected to large loads, such as femoral bones, hip joints and teeth roots.

The main criterion considered for an artificial material to be used as a bone substitute is that it exhibits bioactivity, i.e., an ability to bond with bones in the body, more specifically, the material's capability of forming on its surface an apatite layer of the same type as the inorganic components in bone.

Conventionally employed materials for a bone substitute which exhibit such a characteristic are: $Na_2O$—$CaO$—$SiO_2$—$P_2O_5$ glass, sintered hydroxyapatite ($Ca_{10}(PO_4)_6(OH)_2$), and $MgO$—$CaO$—$SiO_2$—$P_2O_5$ glass-ceramic. These are superior materials having a bioactivity sufficient to form, in the body, an apatite layer on their surface similar to the inorganic components in bone, and thereby can bond with bones directly. However, the values of fracture toughness, i.e., ultimate strength, of such materials (1 to 2 $MPam^{1/2}$) are not nearly comparative to that of a human cortical bone (2 to 6 $MPam^{1/2}$); therefore, they may not be utilized as a substitute material for reconstruction, replacement or repair of hip joints and tibial bones where a large load is applied.

Therefore, the substitute materials currently utilized for large loads are titanium and its alloys which exhibit the most superior biocompatibility among the metallic materials. These metallic materials exhibit a high fracture toughness; however, an extraordinarily long time, about ten years, is required to directly bond these materials to bones. Thus, to shorten the bonding times, bioactivity has been provided to these titanium materials, by the method of plasma coating, so as to cover their surface with molten hydroxyapatite. The materials obtained by this method offer both the fracture toughness of titanium and the bioactivity of apatite.

However, there are the following problems involved in the use of plasma coating: (1) the necessity of an expensive device for the delivery of the plasma spray, (2) the difficulty of controlling the composition and the crystallinity of the hydroxyapatite formed on the metallic substrate surface since the sprayed hydroxyapatite powder is instantaneously, but only once, exposed to about a 30,000° C. level of high temperature, (3) the difficulty of forming a dense apatite layer since the method deposits the half-molten hydroxyapatite powder on the substrate only by free fall, and (4) the difficulty of forming a strong bond of the apatite layer to the substrate due to the preceding reason.

SUMMARY OF THE INVENTION

An object of the present invention is to provide a process which avoids the conventional problems associated with plasma coating.

Another object is to provide a bone repairing material, which provides both the fracture toughness of titanium and the bioactivity of apatite, wherein titanium and apatite are tightly bonded.

Upon further study of the specification and appended claims, further objects and advantages of this invention will become apparent to those skilled in the art.

To achieve the above objects, the material for a bone substitute of the present invention comprises a substrate made of titanium (Ti) or titanium alloys, said substrate having a primary surface layer comprising a titanium oxide phase and amorphous phases of alkali titanates, said primary surface layer having been treated so as to provide a stabilized amorphous alkali titanate layer and a concentration gradient of alkali and titanium ions sufficient to permit apatite from natural or simulated body fluid to be grown thereon. In addition, the material is optionally provided with a second layer, of which the main constituent is apatite, on top of the primary surface layer.

As a substrate, pure Ti is desirable from the viewpoint of biocompatibility, while alloys thereof such as, for example, Ti-6Al-4V, Ti-6Al-4V, Ti-5Al-2.5 Sn, Ti-3Al-13V-11Cr, Ti-15Mo-5Zr-3Al, and Ti-6Al-2Nb-Ta, are preferred because shapes can be more easily fabricated therefrom.

A desirable type of primary surface layer has a gradually decreasing concentration of the titanium oxide phase towards the outer surface, along with a gradually increasing concentration of the total alkali ions towards the outer surface. The desirable thickness of the primary surface layer is about 0.1 to 10 µm, preferably about 1 µm, while that of the second layer is preferably at least 1 µm up to about 10 µm.

A suitable production method to prepare said materials for a bone substitute comprises soaking the substrate made of titanium (Ti) or titanium (Ti) alloys in an alkaline solution optionally under pressure, followed by heating of the resultant substrate to a level of at most the titanium (Ti) or titanium alloys transition temperature. In addition, after the heat treatment, the substrate may be soaked in an aqueous solution which contains calcium (Ca) and phosphorous (P) to a level of, at least, the apatite solubility, such as the simulated body fluid.

Here, the alkaline solution is desirably an aqueous solution which contains at least one of the following ions: sodium ions $Na^+$, potassium ions $K^+$, and calcium ions $Ca^{2+}$. The heating temperature is desirably from 300° to 800° C., and more preferably from 550° to 650° C.

Originally, there exists an extremely thin film on the surface of the titanium (Ti) or titanium (Ti) alloys, which comprises oxides similar to $TiO_2$. $TiO_2$ is an amphoteric substance which reacts with both strong acids and bases. Therefore, soaking of the substrate made of titanium or titanium alloys in an alkaline solution results in the amorphous alkali titanates on the substrate surface with a concentration gradient gradually increasing from the inside where very little reaction takes place, to the outside, where more reaction occurs. The operating conditions of the soaking step, i.e., concentration of alkali, temperature and time, are sufficient to form the amorphous alkali titanates and can vary widely. The formation of the amorphous titanates can be observed visually—a yellow color. Preferred operating conditions are: concentration of alkali—about 1 to 10 molar; temperature—about 40° to 70° C.; and time of reaction—about 1 to 24 hours.

After the soaking step, the substrate is heated to a level of at most the titanium or titanium alloy transition temperature, which causes the diffusion of oxygen and increases the thickness of the said formed phase.

Without being bound by an explanation of the mechanism of the invention, by this method, the surface layer consisting essentially of the titanium oxide phase and the amorphous alkali titanate phase is formed on the surface of the substrate. In addition, the alkali titanate produced by the process exhibits a gradual concentration gradient, wherein the alkali titanate concentration gradually increases towards the outside along the surface thickness direction. Therefore, the titanium oxide phase, the starting material of the said compound, gradually decreases towards the outside. On the other hand, the total concentration of alkali ions ($Na^+$, $K^+$, and $Ca^{2+}$ and so on) in the amorphous alkali titanate phase, increases gradually towards the outside. The slopes of these concentration changes are so gradual that the interface between the substrate and the surface layer and the boundaries among the phases within the surface layer are tightly bonded. This is the major difference from the prior art where the substrate is soaked into a preliminary prepared titania gel in order to form a gel which easily bonds to bones on the Ti surface, but because the adhesive strength between the Ti and the gel layer is weak, the layer can be peeled off. In the present invention, the outer surface is rich in alkali ions, which can be exchanged with hydrogen ions within a simulated or actual body fluid, to form a titanium hydroxide phase which readily reacts with calcium (Ca) and phosphorous (P). In other words, the heat treatment, preferably after the alkali treatment, is effective in stabilizing the amorphous alkali titanate layer and the concentration gradient of alkali and titanium ions, thereby permitting the growth of apatite thereon.

To form apatite, there are used aqueous simulated or body fluids which comprise calcium (Ca) and phosphorus (P) at a concentration at least equal to that of the apatite's solubility. Therefore, such fluids are theoretically capable of growing apatite crystals. However, in reality, the activation energy for the nucleation of the apatite is so high as to prevent spontaneous nucleation of the apatite in the solution or the body fluid. On the other hand, the amorphous titanium hydroxide phase formed by the hydration of alkali titanate phase is highly reactive owing to its amorphous structure. Therefore, it forms apatite nuclei by reacting with the bone forming components in the body fluid. See "The Role of Hydrated Silica, Titanium, and Alumina in Inducing Apatite on Implants," P. Li et al., *J. Biomed. Mater. Res.* 28 (1994) 7–15. Further, apatite nuclei may be preliminarily formed by being soaked into the aqueous solutions, more desirably the simulated body fluids, which consist of calcium (Ca) and phosphorous (P) at a level of at least the apatite's solubility, after the heat treatment. Those materials particularly treated by the simulated body fluid which possess an ion concentration close to that of the body fluid easily bond with bones, since the composition and the structure of the apatite formed on the surface is very similar to those of bones.

With respect to the parameters of the heat treatment, a heat treatment temperature of less than 300° C. generally will not permit diffusion of oxygen into the material at a satisfactory rate, thereby leading to an insufficiency of oxygen in the surface layer. As a result, the primary surface layer will not be thick enough and its ability to form apatite on its surface in the body will be inferior. Conversely, a temperature over 800° C. is undesirably close to the transition temperature of Ti which is 885° C. for pure Ti. When the transition takes place in the Ti or Ti alloy substrate, its mechanical strength deteriorates. Consequently, the temperature range is generally 300°–800° C., preferably 550° to 650° C. The time of heating is sufficient to cause diffusion of oxygen and alkali into the interior of the substrate, and is generally about 1 to 24, preferably 1 to 5 hours. The heating atmosphere is a gas comprising oxygen, typically air.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents, and publications cited above and below and of corresponding Japanese Patent Application No. 5-304659, filed Nov. 9, 1993, is hereby incorporated by reference.

EXAMPLES

Titanium metal plates of 15×10×1 mm size were polished with #400 diamond paste, washed with acetone and subsequently with distilled water. These plates were soaked in either 10 M—NaOH or —KOH aqueous solutions at 60° C. for 24 hours. Then, these test plates were washed with distilled water using a sonic cleaner for at least 20 minutes. Their surfaces were observed to be of a uniform yellow tint and of a uniform yellow for the plates soaked in NaOH and KOH, respectively, which confirmed the formation of alkali titanates.

Then, the Ti metal plates were placed in a furnace and the temperature was raised to 400°, 500°, 600°, and 800° C. at a heating rate of 5° C./min, and maintained at these given temperatures for an hour. The changes in the surface structure of the titanium metal plates after the said treatments were observed by the methods of thin film X-ray diffraction and scanning electron microscope-energy dispersive X-ray analysis (SEM-EDX).

In the thin-film X-ray diffraction pattern of the test plates after being soaked in alkali solutions, broad peaks caused by the amorphous phase were observed at a $2\theta$ value between 23° and 30°. The formation of this phase is attributed to the reaction between titanium oxide and alkali ions. As the temperature of the plate heat treatment increases, the intensity of the titanium oxide crystalline phase peak also increased in the X-ray diffraction. When the heating temperature is at most 600° C., there existed also the peaks of the amorphous phase. On the other hand, the heat treatment at 800° C. resulted in the disappearance of the amorphous phase peak, and, instead, many peaks of crystalline titanium oxide and alkali titanates appeared. On the surface of the test plate which was heat treated at 600° C., there was about a 1 µm thickness of an amorphous layer, which covered the surface of the titanium metal uniformly. Further, the cross-section SEM-EDX observation of the test plate which was heat treated at 600° C. after soaking in KOH solution revealed that the concentration of potassium gradually decreases from the surface to the inside of the amorphous layer. These results are summarized in Table 1.

TABLE 1

| No. | Kind of Alkali Solution | Heating Temp. (°C.) | Constitution Phase of the Primary Surface Layer | Appearance |
|---|---|---|---|---|
| 1 | NaOH | 400 | Ti + Amorphous $TiO_2$ + Amorphous alkali titanate | Uniform |
| 2 | NaOH | 500 | Ti + Rutile + Amorphous $TiO_2$ + Amorphous alkali titanate | Uniform |

TABLE 1-continued

| No. | Kind of Alkali Solution | Heating Temp. (°C.) | Constitution Phase of the Primary Surface Layer | Appearance |
| --- | --- | --- | --- | --- |
| 3 | NaOH | 600 | Ti + Rutile + Amorphous alkali titanate | Uniform |
| 4 | NaOH | 800 | Ti + Rutile + $Na_2Ti_5O_{12}$ | Uniform |
| 5 | KOH | 400 | Ti + Amorphous $TiO_2$ + Amorphous alkali titanate | Uniform |
| 6 | KOH | 500 | Ti + Anatase + Amorphous $TiO_2$ + Amorphous alkali titanate | Uniform |
| 7 | KOH | 600 | Ti + Anatase + Amorphous alkali titanate | Uniform |
| 8 | KOH | 800 | Ti + Anatase + $K_2Ti_5O_{12}$ + $K_2TiO_3$ | Uniform |

As seen in Table 1, the crystalline titanium oxide phases (a rutile type and an anatase type) and amorphous alkali titanate phases are present on the surface of the Ti metal plates which were heat-treated at temperatures from 400° to 600° C. At 400°, there is no crystalline phase of $TiO_2$; but, at this temperature, the densification of the hydrated surface layer is significantly delayed. Thus, the presence of a crystalline form of $TiO_2$ at 500° and 600° is relatively unimportant compared to the increased rate of densification. On the other hand, at 800° C., the amorphous alkali titanate phase has disappeared from the heated Ti metal surface, and the crystalline phase of $Na_2Ti_5O_{12}$ was confirmed, instead.

Then, the obtained test plates were soaked into a simulated body fluid which consists of an inorganic ion concentration almost equal to human body fluid, and the formation of apatite layer was examined. The simulated body fluid was prepared by having the following ion concentrations: $K^+$, 5.0; $Na^+$, 142; $Mg^{2+}$, 1.5; $Ca^{2+}$, 2.5; $Cl^-$, 148; $HCO_3-$, 4.2; $HPO_4^{2-}$, 1.0; and $SO_4^{2-}$, 0.5; each in mM units, and by having its pH value controlled to 7.4 at 37° C. by tri-(hydroxy methyl)-aminomethane and hydrochloric acid.

DETAILED DESCRIPTION OF THE FIGURE

Figure 1:
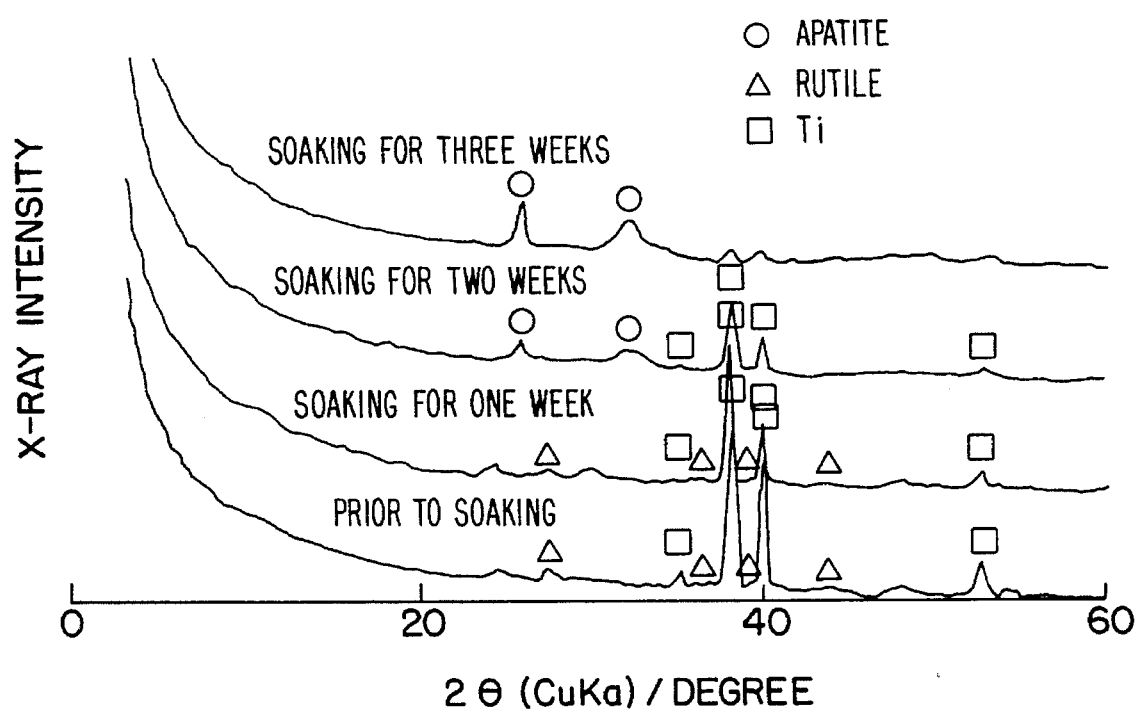
FIG. 1 is a graph indicating the results of thin film X-ray diffraction analysis performed on the test plates which were heat-treated at 600° C. after being soaked in the NaOH solution, then soaked into the simulated body fluid.

FIG. 1 indicates the result of thin film X-ray diffraction analysis performed on the test plates which were heat-treated at 600° C. after being soaked in the NaOH solution, then subsequently soaked into the simulated body fluid. Within two weeks of soaking, apatite started to grow on the surface. After three weeks, the grown apatite layer covered the surface and the titanium metal peaks were hardly observed. After soaking for three weeks, the apatite layer with a 5 to 10 μm thickness formed on the surface of the titanium metal homogeneously. The same tendency was also observed for test plates heat-treated at 400° C. and 500° C.

In summary, the invention has several advantages. First, the manufacturing process involves a simple heating after soaking the Ti metal or Ti alloy into the alkali solution, thereby avoiding any expensive device such as that used for plasma coating. When this material is inserted in the body, the apatite, which is the same as the inorganic components in bones, forms naturally on its surface. Through the apatite, the material bonds with bones tightly. Further, when the material is soaked in an aqueous solution which comprises calcium ions and phosphorous ions at a level which exceeds the saturated concentration of apatite, or preferably in a simulated body fluid, the apatite, which is the same as the inorganic components in bones, forms on the material's surface. Through the apatite, the material bonds with bones tightly. Consequently, this material is superior in biocompatibility.

In addition, because the substrate made of Ti metal or a Ti alloy and the second surface layer made of apatite bond through a primary surface layer made by means of chemical bonding, the adhesive strength of apatite towards the substrate is large. Furthermore, the primary surface layer results from a concentration gradient of components into the metal, thereby providing a very strong bond to the surface layer, resulting in a product having such a high tensile strength that it is useful for high load applications.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A bone repairing material comprising a substrate of titanium or a titanium alloy and on the surface of the substrate a primary surface layer comprising a titanium oxide phase and an amorphous phase of alkali titanate, said primary surface layer thereby forming an interface between said substrate and primary surface layer, said primary surface layer having an interior and an outer surface, said primary surface layer comprising a titanium oxide phase and an amorphous phase of alkali titanate, said primary surface layer having been treated so as to provide a layer comprising amorphous alkali titanate phase and a sufficient concentration gradient of alkali and titanium ions to permit apatite from natural or simulated body fluid to be grown thereon and wherein the concentration of titanium oxide phase in the primary surface layer gradually decreases from the layer interior towards the outer surface, while the concentration of the total alkali ions in the primary surface layer gradually increases from the layer interior towards the outer surface, and wherein said interface between said substrate and said primary surface layer and boundaries of the phases within the surface layer are tightly bonded, said primary surface layer having been heated in a gas comprising oxygen to from about 300° C. to not more than the titanium or titanium alloy transition temperature, for about 1 to 24 hours.

2. A material according to claim 1, further comprising a layer of apatite on top of the said primary surface layer.

3. A material according to claim 1, wherein the thickness of the primary surface layer is 0.1 to 10 μm.

4. A material according to claim 2, wherein the thickness of the primary surface layer is 0.1 to 10 μm.

5. A material according to claim 2, wherein the thickness of the apatite layer is at least 1 μm.

6. A method of producing a material useful as a bone substitute comprising heating a substrate of titanium or titanium alloy and on the surface of the substrate a primary surface layer comprising a titanium oxide phase and an amorphous phase of alkali titanate, said primary surface layer thereby forming an interface between said substrate and primary surface layer, said primary surface layer having an interior and an outer surface, said primary surface layer comprising a titanium oxide phase and an amorphous phase of alkali titanate, said primary surface layer having been treated so as to provide a layer comprising amorphous alkali titanate and a sufficient concentration gradient of alkali and titanium ions to permit apatite from natural or simulated body fluid to be grown thereon and wherein the concentration of titanium oxide phase in the primary surface layer gradually decreases from the layer interior towards the outer surface, while the concentration of the total alkali ions in the primary surface layer gradually increases from the layer interior towards the outer surface, and wherein said interface between said substrate and said primary surface layer and boundaries of the phases within the surface layer are tightly bonded, said heating being conducted in a gas comprising oxygen to a temperature from about 300° C. to not more than the titanium or titanium alloy transition temperature, for about 1 to 24 hours.

7. A method according to claim 6, further comprising soaking the resultant product in an aqueous solution comprising calcium and phosphorous in a concentration level of, at least, apatite solubility.

8. A method according to claim 6, wherein the amorphous alkali titanate phase was formed by soaking the titanium or titanium alloy in an alkaline solution containing at least one of: sodium ions $Na^+$, potassium ions $K^+$, and calcium ions $Ca^{2+}$.

9. A method according to claim 6, wherein the heating temperature is from 300° to 800° C.

10. A method according to claim 6, wherein the heating temperature is from 550° to 650° C.

11. A method according to claim 9, wherein the heating is conducted for about 1–24 hours.

12. A method according to claim 10, wherein the heating is conducted for about 1–24 hours.

13. A material according to claim 1, wherein the heating temperature is from 300° to 800° C.

14. A material according to claim 1, wherein the heating temperature is from 550° to 650° C.

* * * * *